United States Patent [19]
Yonezawa

[11] Patent Number: 6,021,935
[45] Date of Patent: Feb. 8, 2000

[54] GLOVE RELEASE APPARATUS AND METHOD FOR THE SAME

[76] Inventor: Narimitsu Yonezawa, 601, 1-31, Asakusabashi 5-chome, Taito-ku, Tokyo 111, Japan

[21] Appl. No.: 08/874,718

[22] Filed: Jun. 13, 1997

[30] Foreign Application Priority Data

Jun. 14, 1996 [JP] Japan .................................. 8-153785

[51] Int. Cl.[7] .............................................. A47G 25/80
[52] U.S. Cl. ............................................................ 223/111
[58] Field of Search ................................. 223/111, 43, 1, 223/78, 79, 80

[56] References Cited

U.S. PATENT DOCUMENTS

| | | | |
|---|---|---|---|
| 3,067,001 | 12/1962 | McCollum | 223/111 |
| 4,085,519 | 4/1978 | Masika | 223/79 |
| 4,876,747 | 10/1989 | Coffey et al. | 223/111 |
| 4,898,309 | 2/1990 | Fischer | 223/111 |
| 4,915,272 | 4/1990 | Vlock | 223/111 |
| 5,058,705 | 10/1991 | Rich et al. | 223/111 |
| 5,658,353 | 8/1997 | Layton | 223/111 |

*Primary Examiner*—Bibhu Mohanty
*Attorney, Agent, or Firm*—Liniak, Berenato, Longacre & White

[57] ABSTRACT

Since surgical gloves contact patients' blood and focuses, there is a possibility of infection, especially the case of Hepatitis B virus and AIDS if hands contact blood on the gloves. Therefore, a glove release apparatus of the present invention is for safely and sanitarily pulling off a glove made of a stretchable material from a hand and comprises a housing having an opening to which the hand wearing the glove is inserted, and an engagement unit for hooking an insertion opening of the glove, please near the opening of the housing. In order to pull off the glove, the hand wearing the glove is inserted into the opening of the housing and the insertion opening of the glove is hooked to the engagement unit. Then, as the hand is moved towards the opening of the housing, the glove is gradually pulled off from the hand.

14 Claims, 7 Drawing Sheets

4a 4a
4a
4a

GLOVE RELEASE APPARATUS AND METHOD FOR THE SAME

BACKGROUND OF THE INVENTION

1. Field of the Invention

The present invention relates to a glove release apparatus and a method for the same, which easily and sanitarily pulls off gloves made of stretchable members such as natural rubber or synthetic rubber from hands.

2. Description of Related Art

Stretchable gloves are usually used during surgeries. Gloves used in hospitals are made thin so as to fit fingers for delicate operations with medical instruments. There is strict sanitary control for use of gloves since surgeons perform operations on incised body with gloves on. When the surgeon puts on the gloves, hands are washed and brushed with medicated soap and dried with a drier, and then a nurse who already finishes sterilization puts gloves on the surgeon's hands against the elasticity of gloves so that the fingertips of the glove reach the surgeon's fingertips.

Further, to pull off the gloves from hands after surgeries, the glove is pulled off with the other hand wearing the glove on and then the other glove is pulled off with the other bear hand.

However, there arises the following problem in this conventional glove release method.

Since surgical gloves contact patients' blood and focuses, there is a possibility of infection, especially the case of Hepatitis B virus and AIDS if hands contact blood on the gloves.

BRIEF SUMMARY OF THE INVENTION

It is an object of the present invention to provide a glove release apparatus and a method for the same which can easily and sanitarily pulling off gloves without hurting hands and without touching surfaces of used gloves with hands.

In order to achieve the above object, a glove release apparatus of the present invention comprises a housing having an opening to which the hand wearing the glove is inserted, and an engagement unit for hooking an insertion opening of the glove, placed near the opening of the housing.

With this configuration, as the hand is moved towards the opening of the housing, the glove can easily be pulled off from the hand without touching a surface of the glove. Accordingly, safety is achieved, e.g., for a surgeon performing an operation.

Further, the engagement unit may be formed into a first protrusion. An injection hole can be provided at the first protrusion, and a fluid injection device is connected to the injection hole.

Then, fluid such as water and air is injected from the protrusion and the hand is moved so that the glove is pulled off. Accordingly, the fraction between the hand and glove is decreased and the glove is more readily pulled off from the hand.

In the glove release apparatus of the present invention, the engagement unit may be fixed near the opening of the housing. Alternatively, the engagement unit may be reciprocated so as to be close to and apart from the insertion opening of the glove using a traveling mechanism for moving the engagement unit and switch for turning on the traveling mechanism.

In this case, when the hand wearing the glove is inserted into the housing from the opening, the engagement unit is moved towards the hand to hook the glove. While the glove is hooked to the engagement unit, as the hand is moved towards the opening, the glove is readily pulled off.

Further, in the glove release apparatus of the present invention, another protrusion having a blade for cutting a glove can be placed opposing to the engagement unit.

With this configuration, the glove is cut from the one surface, which decreases the fraction between the glove and hand and which makes the release of glove easier. If the fluid is injected from the protrusion, the glove is more readily pulled off from the hand.

Further, it is preferable that the blade comprises an approach preventing guide for preventing a hand from touching the blade, provided near the blade, and a suction hole for a suction mechanism.

With this configuration, the hand never touches the blade because there is the approach preventing guide and the glove is sucked by the suction mechanism while the glove is cut.

Further, according to a method for pulling off a glove from a hand of the present invention comprises steps of hooking an insertion opening of the glove made of a stretchable material to an engagement unit, and moving a hand towards the engagement unit to pull off the glove from the hand.

Here, fluid may be injected into the glove from an injection hole of the engagement unit while the hand is moved towards the engagement unit.

PREFERRED EMBODIMENTS OF THE INVENTION

Figure 1:
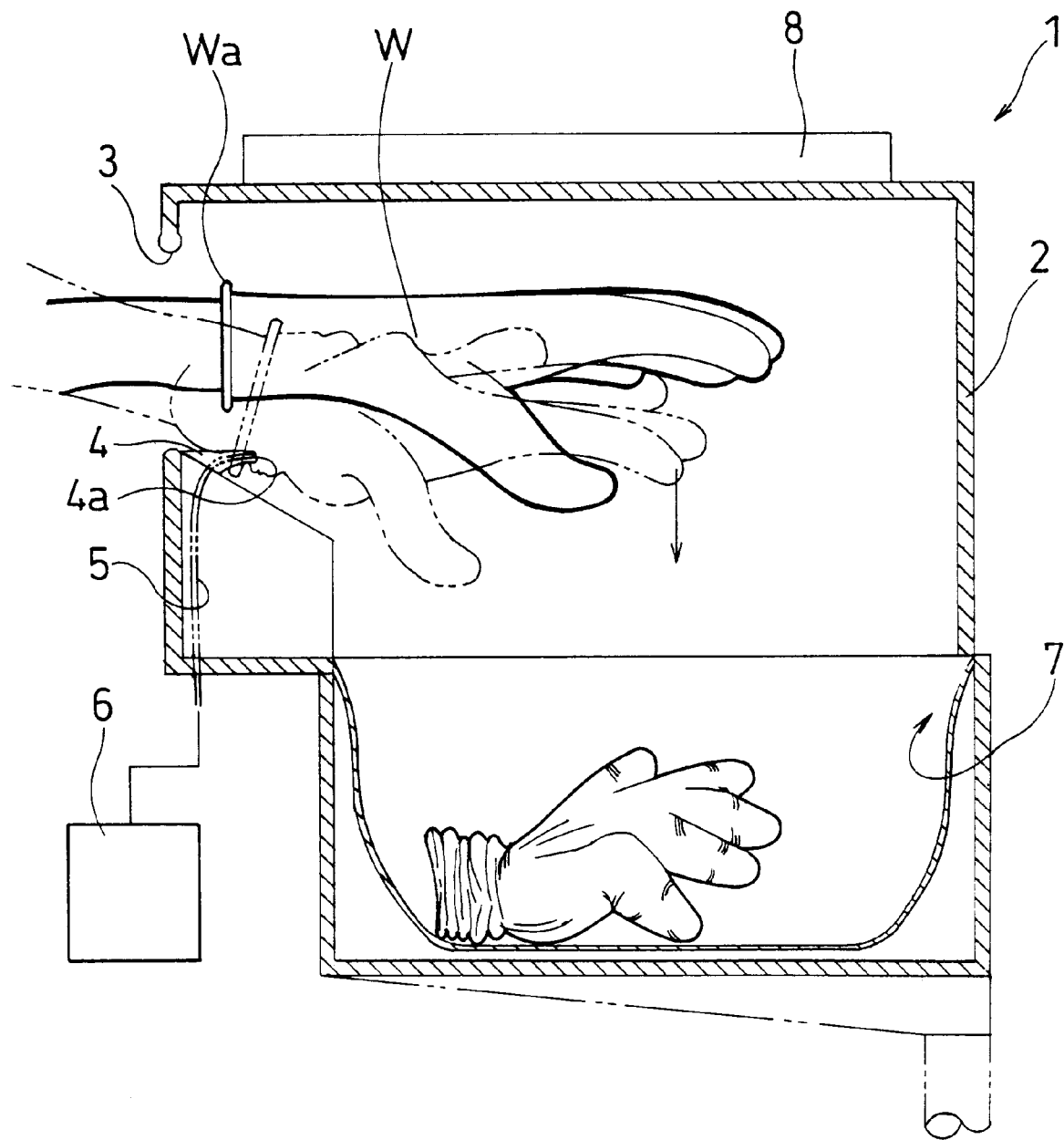
FIG. 1 is a sectional view showing a main portion of a glove release apparatus according to the first embodiment of the present invention.

The preferred embodiments of the present invention will be described hereinafter with reference to the accompanying drawings. In the following description and the drawings, the same reference numerals are used for the same components and repetitive description will be omitted.

Figure 2A:
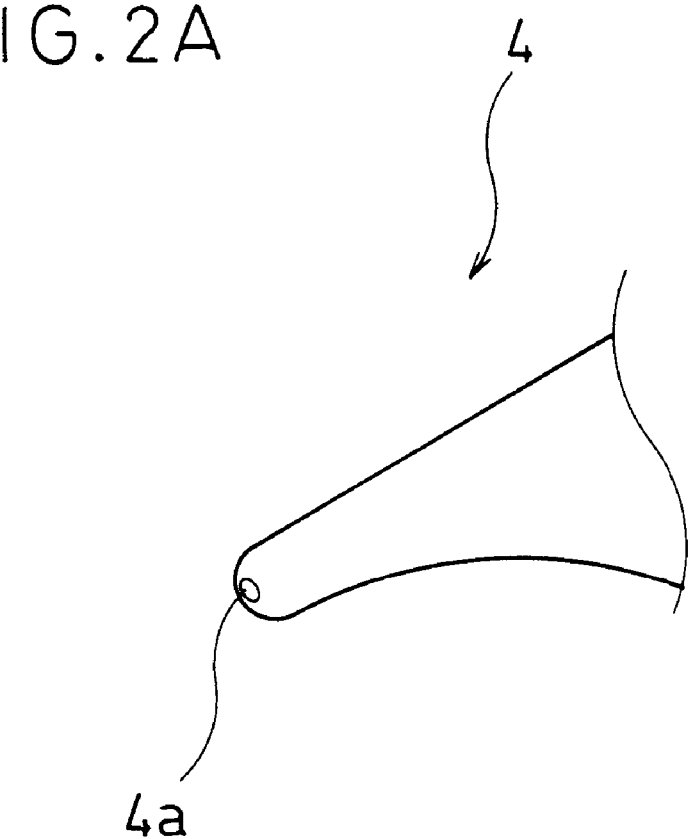
FIG. 2A is a perspective view showing the structure of an engagement part of the glove release apparatus of FIG. 1.
Figure 2B:
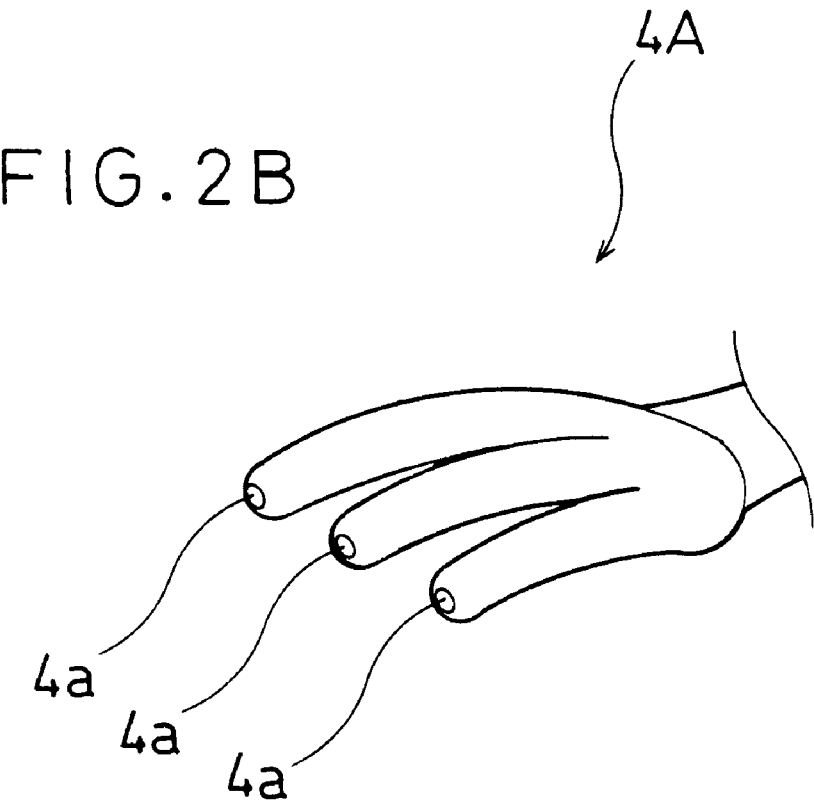
FIG. 2B is a perspective view showing the modified structure of an engagement part of the glove release apparatus of FIG. 1.

FIG. 1 is a sectional view showing a glove release apparatus according to the first embodiment of the present invention. FIG. 2A and FIG. 2B are perspective views showing the structure of an engagement unit.

As shown in FIG. 1, the glove release apparatus 1 comprises a housing 2 having an opening 3, a protrusion 4 as an engagement unit placed near the opening 3, an injection hole 4a formed at the tip of the protrusion 4, a fluid injection device 6 communicated with the injection hole 4a through a supply pipe 5, a storage unit 7 provided at the bottom of the housing 2, and a germicidal lamp 8 at a predetermined portion of the housing 2.

It is preferred that the protrusion 4 has a curved surface as shown in FIG. 2A and that the end portion is formed thin so as to be easily inserted into an insertion opening Wa between a hand and a glove W. Alternatively, as shown in FIG. 2B, the protrusion 4 can be formed as a protrusion 4A having a plurality of branches (in FIG. 2, three). In the case of protrusion 4A, an injection hole 4a can be provided at the tip of each branch or at least at the tip of a central branch.

Fluid injected from the injection hole 4a of the protrusion 4 may be gas such as air or liquid such as water. In the case of liquid injection, a plurality of through holes are formed at the storage unit 7 so that the liquid is collected in a storage tank through the through holes. Alternatively, a drain pipe is provided so that liquid flows into sewage as shown by a chain double-dashed line in FIG. 1. Further, it is preferred that a switch may be provided either outside or inside the housing 2 to inject the fluid. Furthermore, it is preferred that the fluid injection can be controlled so that injection continues for certain time, e.g., ten seconds and then terminated, and that a sensor switch such as a photo sensor is provided at the opening 3 so that the injection starts when the hand is inserted and the injection is terminated when the hand is pulled out.

Next, the operation of the glove release apparatus 1 will be described.

First, as shown in FIG. 1, the hand wearing the glove W is inserted into the housing 2, and the insertion opening Wa of the glove W is hooked to the protrusion 4. Next, the fluid injection device 6 is operated by the switch, and while the fluid such as air and water is injecting, the hand is moved in a direction that the hand is pulled out from the housing 2. Then, the glove W is gradually pulled off from the palm and the back, and pulled off from the fingers by the fluid injection. As the hand is further moved towards the opening 3 of the housing 2, the glove W is completely pulled off from the hand.

The protrusion 4 acts for suppressing the fraction between the hand and glove and avoiding the fraction by injecting fluid between the hand and glove in order to smoothly pull off the glove. Further, if the fluid is injected with strong force, the glove W can more easily be pulled off from the hand.

When the glove W is pulled off from the hand, it falls into the storage unit 7. If the predetermined number of gloves W is collected, the storage unit 7 is drawn from the housing 2 like a drawer, and a bag containing the gloves is removed and a new back is set in the storage unit 7. Then, the storage unit 7 is returned into the housing 2.

It is preferred that the germicidal lamp 8 is provided at the side of the housing 2 and that the top surface of the housing 2 is made of a translucent material which cuts off light having a bad influence to eyes from the germicidal lamp 8 so that the glove can safely be pulled off while a person wearing the glove looks the glove release operation. It should be noted that if the apparatus 1 is not constructed that the fluid is injected from the protrusion 4, the glove still can readily be pulled off with the apparatus 1. Further, in FIG. 1, the protrusion 4 is provided at one place that is the lower portion of the opening 3 but it may be provided at two or more places.

Next, the second embodiment of the glove release apparatus will be described with reference to FIG. 3.

Figure 3:
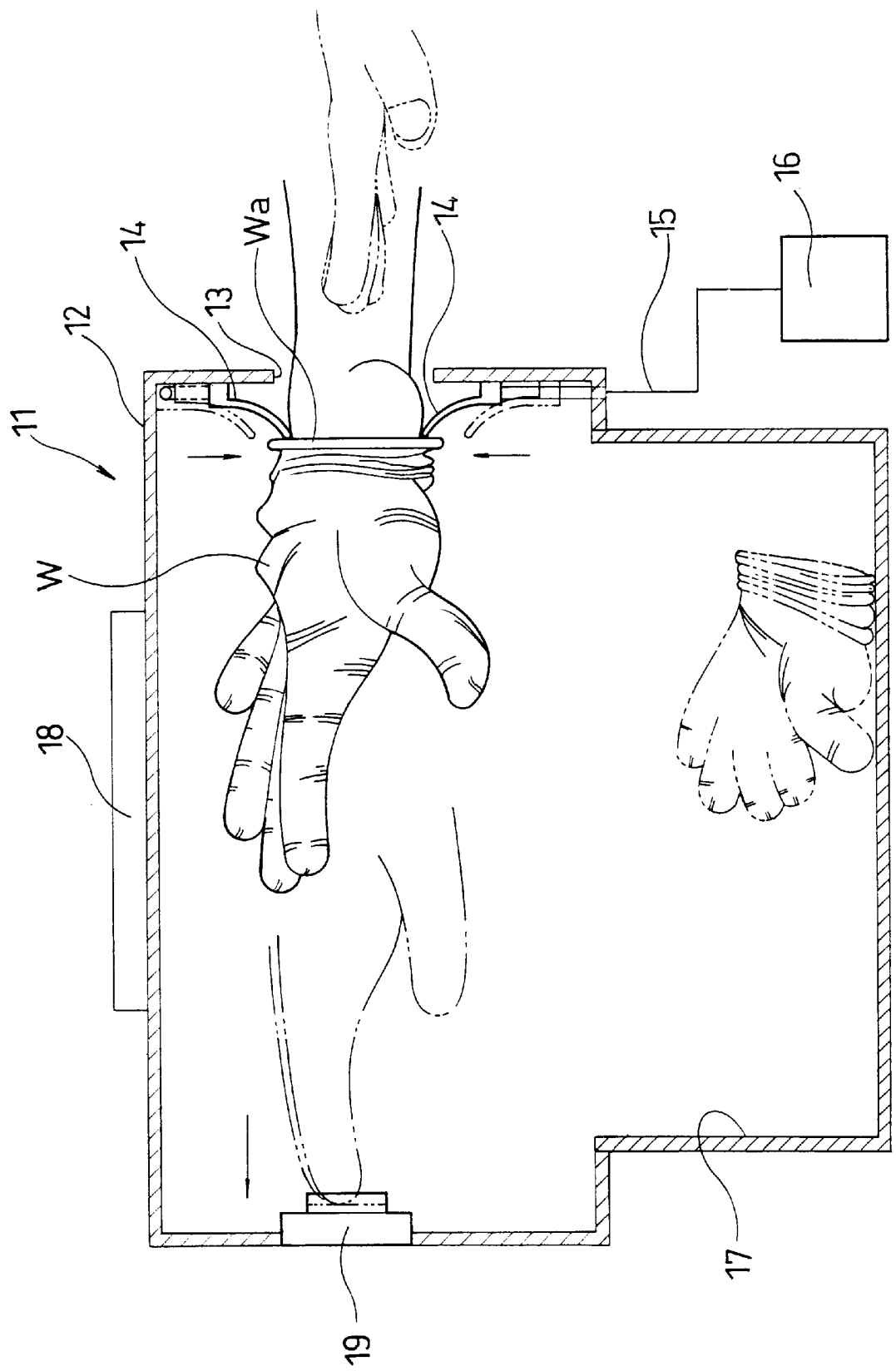
FIG. 3 is a sectional view showing a main portion of a glove release apparatus according to the second embodiment of the present invention.

FIG. 3 is a sectional view of the glove release apparatus according to the second embodiment of the present invention. As shown in FIG. 3, the glove release apparatus 11 comprises a housing 12 having an opening 13, movable protrusions 14 as an engagement unit having an injection hole placed near the opening 13, a switch 19 for operating the protrusions 14, a fluid injection device 16 connected to the injection hole with a pipe 15, a storage unit 17 provided at a space under the housing 12, and a germicidal lamp 18 provided at a predetermined portion of the housing 12. The protrusions 14 may be formed as the one having one protrusion or the one having a plurality of branches as shown in FIG. 2A and FIG. 2B, respectively.

Next, the operation of the glove release apparatus 11 will be described.

As shown in FIG. 3, first, the hand wearing the glove W is inserted into the inner part of the housing 12 and turns on the switch 19. Then, the protrusions 14 move towards hands and stop when they touch the hand in front of the insertion opening Wa. Next, the hand is moved in a direction that the hand is pulled out from the housing 12 to insert the protrusions 14 into the insertion opening Wa of the glove W. When the hand is further moved towards the opening 13 of the housing 12, only the hand is moved towards the opening 13 while the glove W is hooked to the protrusions 14 and pulled off from the hand.

If the apparatus 11 is constructed that the fluid injection device 16 is operated when the protrusions 14 touch the hand by turning on the switch 19, with the insertion opening Wa hooked to the protrusions 14, the glove W is more easily pulled off by the fluid injection such as air and water since the glove W is pushed towards the inner part of the housing 12. In the case that the fluid is liquid such as water and disinfectant, it is preferred that the pipe is provided at the storage unit 17 to flow the liquid into sewage (see the chain double-dashed line in FIG. 1).

Further, it is preferred that a photo sensor is provided at the opening 13, so that the protrusions 14 that has been moved towards the hand are returned to the position shown by the chain double-dashed line in FIG. 3 when the sensor does not detect the hand. In this case, it is further preferred that the fluid injection is terminated by the photo sensor.

Next, referring to FIG. 4, the third embodiment of the glove release apparatus will be described.

Figure 4:
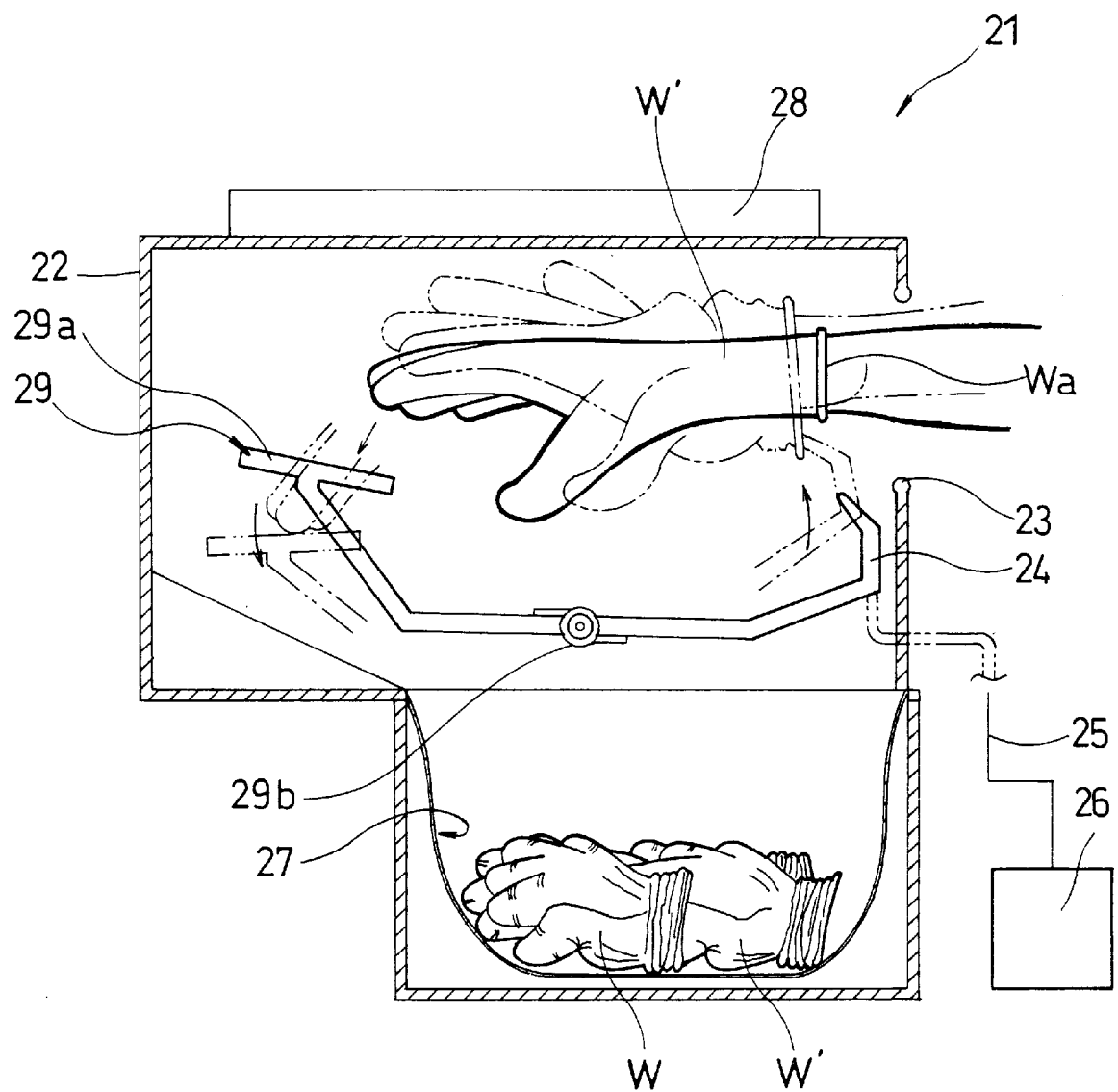
FIG. 4 is a sectional view showing a main portion of a glove release apparatus according to the third embodiment of the present invention.

FIG. 4 is a sectional view of the glove release apparatus according to the third embodiment of the present invention. As shown in FIG. 4, the glove release apparatus 21 comprises a housing 22 having an opening 23, a protrusion 24 as an engagement unit placed near the opening, 3, a switching mechanism 29 integrated with the protrusion 24, a storage unit 27 provided at a space under the housing 22, and a germicidal lamp 28 provided at a predetermined portion of the housing 22.

The switching mechanism 29 comprises a switch plate 29a and a spring coil 29b provided substantially at the middle of the protrusion 24 and the switch plate 29a. The protrusion 24 always receives the elasticity of the spring coil 29b so as to be in position. A fluid injection device 26 may be provided at the protrusion 24 so that fluid such as air and water from the fluid injection device 26 is injected from the tip of the protrusion 24 through a pipe 25.

The operation of the glove release apparatus 21 is as follows.

First, the hand wearing the glove W is inserted into the housing 22 from the opening 23 to move the switch plate 29a lower to hook the protrusion 24 to the insertion opening Wa of the glove W. When the insertion opening Wa is hooked to the protrusion 24, as the hand is moved towards the opening 23 of the housing 22, the glove is pulled off from the hand.

The glove W pulled off from the hand falls into the storage unit 27. When the predetermined number of gloves is collected, the gloves are disposed from the storage unit 27. If, with the fluid injection device 26, fluid is injected from the protrusion 24, the glove W is more easily removed from the hand W.

Next, the forth embodiment of the glove release apparatus will be described with reference to FIG. 5.

Figure 5:
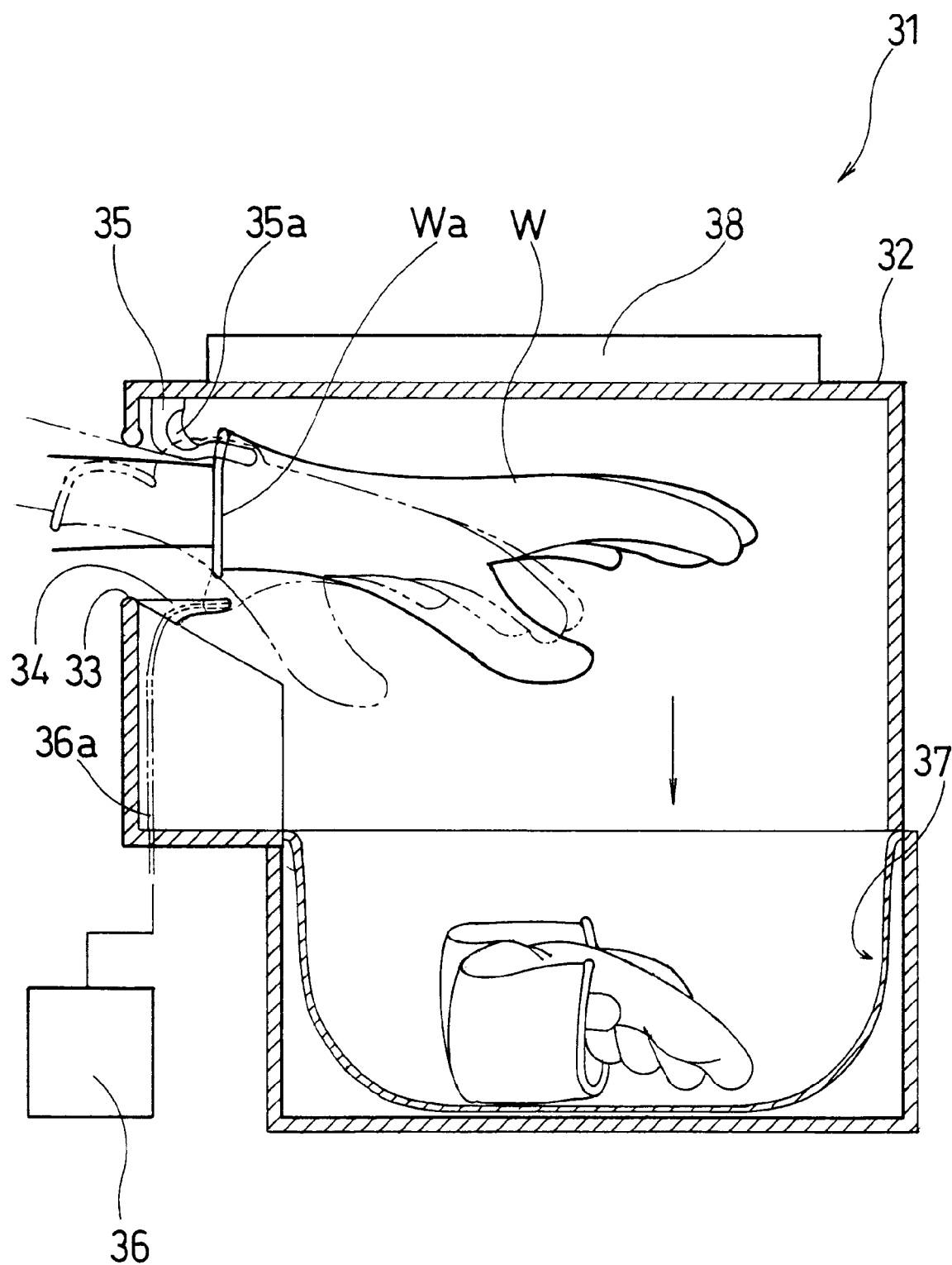
FIG. 5 is a sectional view showing a main portion of a glove release apparatus according to the forth embodiment of the present invention.

FIG. 5 is a sectional view showing the glove release apparatus according to the forth embodiment of the present invention. As shown in FIG. 5, the glove release apparatus 31 comprises a housing 32 having an opening 33, a protrusion 34 as an engagement unit placed at the lower portion of the opening 33, a protrusion 35 placed at the upper portion of the opening 33, and a storage unit 37 provided at the lower portion of the housing 32. The protrusion 35 has a blade 35a facing to the inner part of the housing 32. It is preferred that a fluid injection device 36 may be provided at the protrusion 34 so that fluid such as air and water from the fluid injection device 36 is injected from the tip of the protrusion 34 through a pipe 36a.

The release of the glove W is operated by the following procedure using the glove release apparatus 31.

As shown in FIG. 5, the hand wearing the glove is inserted into the glove release apparatus 31 from the opening 33, and first the upper insertion opening Wa of the glove W is hooked to the upper protrusion 35 and then while the glove is stretched, the lower insertion opening Wa of the glove W is hooked to the lower protrusion 34.

Next, as the hand is moved towards the opening 33 of the housing 32, the glove W is cut by the blade 35a of the upper protrusion 35. Then, the glove is gradually pulled off from the hand while the glove W is hooked to the lower protrusion 34 and the upper protrusion 35 which cuts the glove W. When the finger of the glove is cut by the blade 35a, the glove W is completely pulled off from the hand. Since the glove W is stretched when put on the hand, when the glove W is cut by the blade 35a, the cut portion of the glove W is rolled and pulled off from the hand. Accordingly, the glove W can be pulled off without the dirty surface of the glove W touching the hand.

If the fluid such as air and water is injected from the protrusion 34, the glove W may more easily be pulled off from the hand. The protrusion 35 having a blade 35a does not have to be placed to face the protrusion 34. It may be placed at the any position unless the blade 35a can cut the back of the glove W.

Next, the fifth embodiment of the glove release apparatus will be described with reference to FIG. 6.

Figure 6:
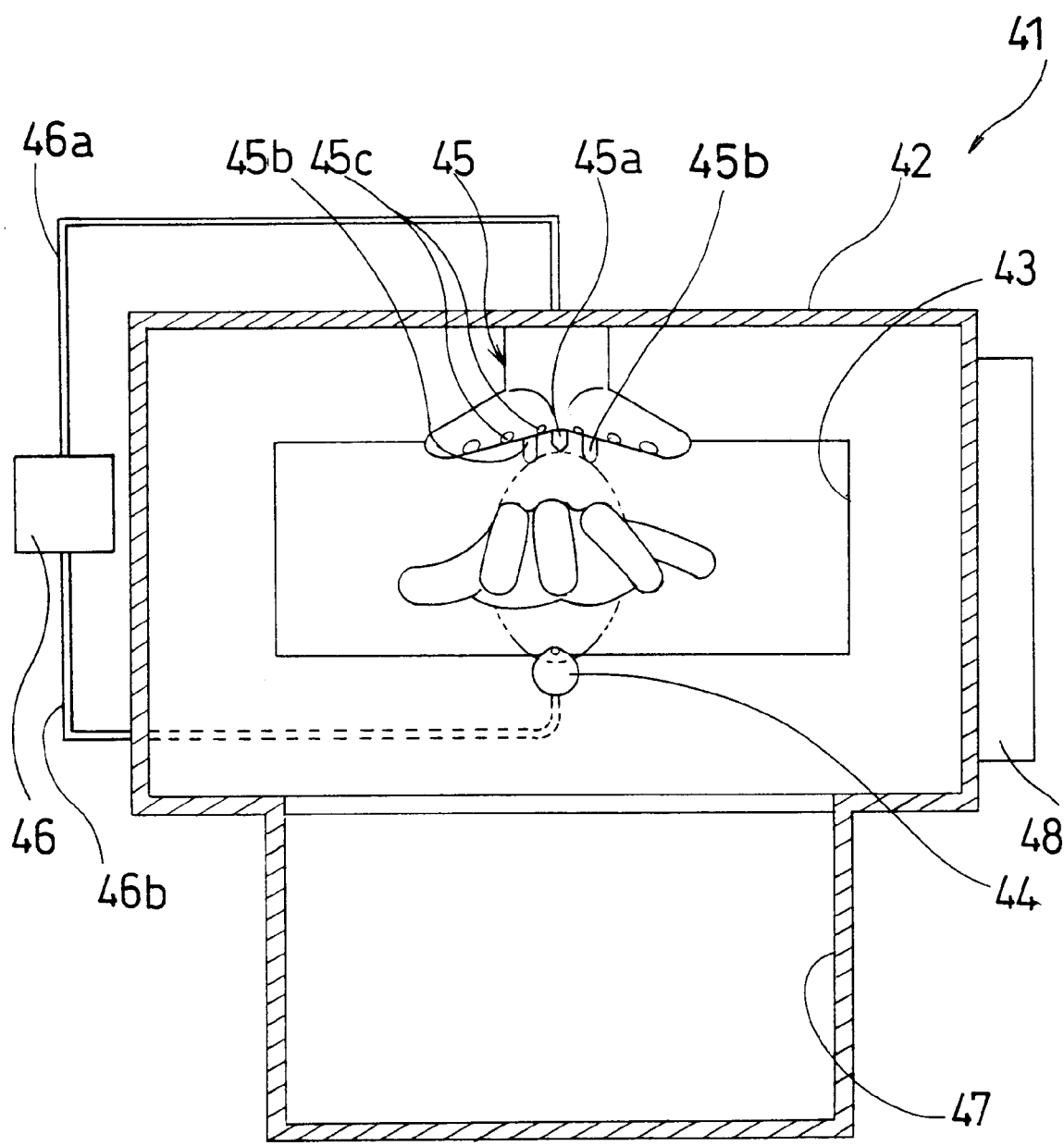
FIG. 6 is a sectional view showing a main portion of a glove release apparatus according to the fifth embodiment of the present invention.

FIG. 6 is a sectional view showing the glove release apparatus according to the fifth embodiment of the present invention. As shown in FIG. 6, the glove release apparatus 41 comprises a housing 42 having an opening 43, a suction cutting unit 45 placed at the upper portion of the opening 43, a protrusion 44 as an engagement unit placed at the lower portion of the opening 43, a storage unit 47 provided at the lower portion of the housing 42, and a germicidal lamp 48 placed at the side of the housing 42.

The suction cutting unit 45 is formed in a reverse Y shape and comprises a blade 45a at a branch and approach preventing guides 45b for preventing a hand from touching the blade 45a at the left and right of the blade 45a, suction holes 45c near the blade 45a and the approach preventing guides 45b. The suction holes 45c are connected to the suction device 46 through a joint pipe 46a.

If an injection hole is provided at the protrusion 44 and the fluid, especially air is injected from the protrusion 44, it is preferable that the air sucked by the suction device 46 is injected from an injection hole of the protrusion 44 through a pipe 46b. Further, the approach preventing guides 45b preferably have a narrower width than the fingers.

The operation of the glove release apparatus 41 having the above-described structure is as follows.

The hand wearing the glove W is inserted into the housing 42 from the opening 43 so that the insertion opening Wa of the glove W is hooked to the protrusion 44 facing to the palm. Then, the hand is raised towards the suction cutting unit 45 so that the glove W is stretched. Thereafter, the suction device 46 is operated by a sensor switch and sucks air from the suction holes 45c. Accordingly, the glove is sucked as shown by a chain double-dashed line in FIG. 6. At this point, since there is the approach preventing guides 45b, the hand never touches the blade 45a although the hand is moved and the glove W is cut by the blade.

Accordingly, as the hand is moved towards the opening 43 of the housing 42, the glove W is cut by the blade 45a and the area of the glove touching the hand decreases, which decreases the fraction between the hand and the glove. Therefore, the glove is easily pulled off from the hand. It should be noted that if air is injected from the protrusion, the glove is more easily pulled off from the hand.

The preferred embodiments of the present invention have been described above. However, the glove release apparatus of the present invention is not limited to the above-described embodiments.

Figure 7A:
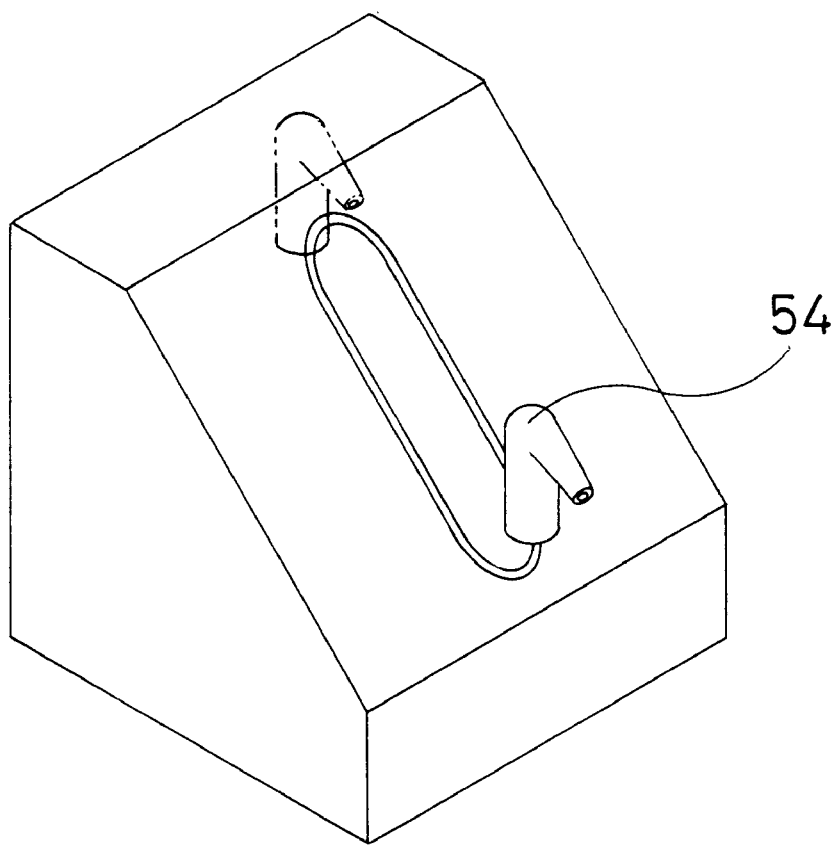
FIG. 7A is a perspective view showing a modified protrusion of the present invention.
Figure 7B:
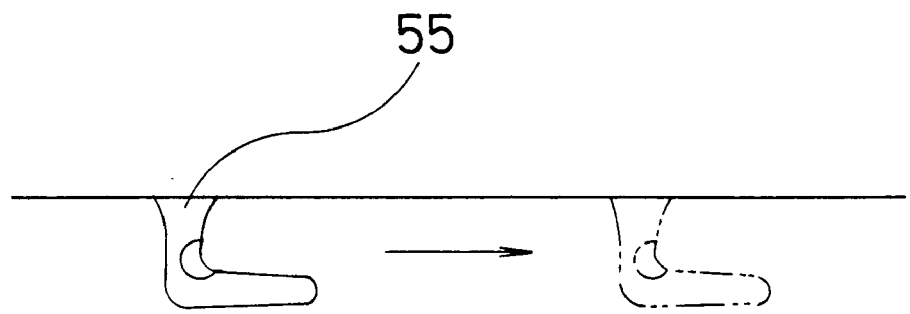
FIG. 7B is a side view showing a modified protrusion of the present invention.

For example, the protrusion used in each glove release apparatus of the preferred embodiments can be formed like one shown in FIG. 7A. Here, the protrusion applied to the first embodiment of the present invention will be explained. A protrusion 54 is provided on an inclined surface, and a raceway groove is formed in the inclined surface. The protrusion 54 is moved along the raceway groove by a traveling mechanism. With this structure, the protrusion 54 is inserted into the glove to hook the glove. Then, the protrusion 54 is moved so as to be apart from the opening of the housing. Accordingly, the glove is readily pulled off from the hand. It should be noted that the protrusion 54 may have an injection hole to inject the fluid, which makes the release of glove more easier. Further, the protrusion having a blade can be formed like a protrusion 55 shown in FIG. 7B that is movable by the traveling mechanism. If the protrusion 55 is used with the protrusion 54, the glove is further readily pulled off from the hand.

Further, in the third embodiment, a support shaft of the switch mechanism 29 can be formed movable, so that the protrusion 24 is moved into the inner part of the housing 22 when the switch plate 29a is operated and the glove W is hooked to the protrusion 24.

Furthermore, the engagement unit including a protrusion may comprise a suction hole placed near the opening of the housing. In this case, as the hand wearing the glove is inserted in the opening of the housing, the glove is sucked through the suction holes and the glove W is readily hooked to the protrusion.

Furthermore, in the glove release apparatus of the above-described preferred embodiments, the structure for pulling off one glove was explained; however, each glove release apparatus can be formed that the both gloves are pulled off at the same time by providing two openings at the housing.

While the invention has been shown and described with reference to the illustrated embodiments, it should be understood that various changes in form and details may be made without departing from the scope of the invention which is defined in the appended claims.

What is claimed is:

1. A glove release apparatus for pulling off a glove made of a stretchable material from a hand comprising:
    a housing having an opening to which the hand wearing the glove is inserted; and
    an engagement unit for hooking an insertion opening of the glove, placed near said opening of said housing, and
    a storage unit slidably provided underneath said housing to store the glove after the glove is removed from the hand.

2. A glove release apparatus for pulling off a glove made of a stretchable material from a hand comprising:
    a housing having an opening to which the hand wearing the glove is inserted; and
    an engagement unit for hooking an insertion opening of the glove placed near said opening of said housing, and
    a storage unit slidably provided underneath said housing to store the glove after the glove is removed from the hand, wherein said engagement unit is formed into a first protrusion and an injection hole is provided at said first protrusion; and a fluid injection device is connected to said injection hole.

3. A glove release apparatus according to claim 1, wherein said engagement unit is fixed near said opening of said housing.

4. A glove release apparatus for pulling off a glove made of a stretchable material from a hand comprising:
    a housing having an opening to which the hand wearing the glove is inserted; and
    an engagement unit for hooking an insertion opening of the glove, placed near said opening of said housing, and
    a storage unit slidably provided underneath said housing to store the glove after the glove is removed from the hand; and said apparatus further comprising a traveling mechanism for moving said engagement unit and a switch for turning on said mechanism;
    said engagement unit being formed in a first protrusion; and
    said first protrusion being reciprocated so as to be close to and apart from said insertion opening of said glove by said traveling mechanism.

5. A glove release apparatus according to claim 1, wherein said engagement unit has a plurality of protrusions.

6. A glove release apparatus according to claim 2, wherein said engagement unit has a plurality of protrusions.

7. A glove release apparatus for pulling off a glove made of a stretchable material from a hand comprising:
    a housing having an opening to which the hand wearing the glove is inserted:
    an engagement unit for hooking an insertion opening of the glove, placed near said opening of said housing: and
    a second protrusion having a blade for cutting the glove, said second protrusion disposed opposite said engagement unit with respect to said opening.

8. A glove release apparatus according to claim 7, wherein said blade comprises an approach preventing guide for preventing a hand from touching said blade, provided near said blade, and a suction hole for a suction mechanism.

9. A method for pulling off a glove from a hand comprising steps of:
    hooking an insertion opening of said glove made of a stretchable material to an engagement unit;
    moving a hand toward said engagement unit to pull off said glove from said hand; and
    injecting fluid into said glove from an injection hole of said engagement unit while said hand is moved toward said engagement unit.

10. A glove release apparatus for pulling off a glove made of a stretchable material from a hand comprising:
    a housing having an opening to which the hand wearing the glove is inserted,
    an engagement unit for hooking an insertion opening of the glove placed near said opening of said housing,
    a storage unit slidably provided underneath said housing to store the pulled off glove,
    a traveling mechanism for moving said engagement unit, and
    a switch for turning on the traveling mechanism.

11. A glove release apparatus according to claim 10, wherein said engagement unit is formed into a first protrusion and an injection hole is provided at said first protrusion and a fluid injection device is connected to said injection hole.

12. A glove release apparatus according to claim 11, further comprising a second protrusion having a blade for cutting a glove, placed opposing to said engagement unit.

13. A glove release apparatus according to claim 11, wherein said blade comprises an approach preventing guide provided near said blade for preventing the hand from touching said blade, and a suction hole for a suction mechanism.

14. A glove release apparatus according to claim 11, wherein said engagement unit has a plurality of protrusions.

* * * * *